(12) United States Patent
Pavlak

(10) Patent No.: US 6,257,719 B1
(45) Date of Patent: Jul. 10, 2001

(54) PROTECTIVE EYEWEAR

(76) Inventor: Ronald M. Pavlak, 1063 Kirkwood Dr., Eagan, MN (US) 55123

( * ) Notice: Subject to any disclaimer, the term of this patent is extended or adjusted under 35 U.S.C. 154(b) by 0 days.

(21) Appl. No.: 09/736,601

(22) Filed: Dec. 13, 2000

Related U.S. Application Data

(63) Continuation of application No. 09/487,650, filed on Jan. 19, 2000.

(51) Int. Cl.$^7$ .................................................. G02C 11/08
(52) U.S. Cl. ............................. 351/62; 351/158; 2/437
(58) Field of Search .......................... 351/41, 44, 62, 351/155, 158; 2/436, 437

(56) References Cited

U.S. PATENT DOCUMENTS

| | | | |
|---|---|---|---|
| D. 321,703 | 11/1991 | Grau | D16/112 |
| D. 358,159 | 5/1995 | Lai | D16/312 |
| D. 366,667 | 1/1996 | Arnette | D16/329 |
| D. 407,428 | 3/1999 | Jannard et al. | 16/6 |
| 2,393,837 | 1/1946 | Swanson | 351/62 |
| 2,496,969 | 2/1950 | Wentworth | 351/62 |
| 3,133,982 | 5/1964 | Janz | 88/41 |
| 3,701,591 | 10/1972 | Wichers | 351/41 |
| 4,240,718 | 12/1980 | Wichers | 351/62 |
| 4,852,189 | 8/1989 | Duggan | 2/452 |
| 4,877,320 | 10/1989 | Holden | 351/44 |
| 4,934,807 | 6/1990 | Bolle et al. | 351/62 |
| 5,239,320 | 8/1993 | Allendrof et al. | 351/62 |
| 5,319,396 | 6/1994 | Cesarczyk | 351/62 |
| 5,495,303 | 2/1996 | Kolentsi | 351/43 |
| 5,576,775 | 11/1996 | Bolle | 351/62 |
| 5,711,035 * | 1/1998 | Haslbeck | 2/436 |
| 5,740,556 | 4/1998 | Brown | 2/181 |

OTHER PUBLICATIONS

"Visual Reality," *Runner's World* p. 72, May 1997.
Zeal Optics ad, no date.

* cited by examiner

*Primary Examiner*—Huy Mai
(74) *Attorney, Agent, or Firm*—Michael S. Sherrill

(57) ABSTRACT

Protective eyewear comprising a standard pair of conventional prescription glasses, protective eyewear, or sunglasses to which a brow bar is attached. The brow bar contains means allowing the attachment of an absorbent insert to be attached, with the insert contacting the wearer's forehead during use. The brow bar contains a plurality of evaporation windows permitting continual evaporation of perspiration generated by the user during activity.

14 Claims, 8 Drawing Sheets

PROTECTIVE EYEWEAR

This is a continuation of U.S. patent application Ser. No. 09/487,650, filed Jan. 19, 2000, now pending.

FIELD OF THE INVENTION

The invention relates to eyewear. More specifically, the invention relates to eyewear for the sports enthusiast.

BACKGROUND

Protective eyewear has been used for years in various sports, including high speed sports such as motorcycle racing, skiing and skydiving, and contact sports such as basketball, hockey and football. More recently, similar eyewear has been used in other sports such as bicycling and running, as well as various leisure activities such as sailing and hiking. In all of these and many other activities, the participant will naturally perspire in an effort by the body to cool itself through evaporation as a result of heat internally generated from accelerated calorie burning. Most parts of the body perspire, including the facial and forehead region. When the forehead perspires, sweat will drip into the eyes, causing a burning sensation when the perspiration reaches the eyes. When wearing eyewear, perspiration can become trapped between the eye-facing surface of the lenses and the face, causing the participant to experience vision obscurities when the lenses fog up.

Several attempts at solving this problem have been proposed. As described in U.S. Pat. No. 4,240,718, a bar is attached to the eyewear frame to maintain a distance between the eyewear and the face. While such an arrangement allows an increased amount of evaporation to take place than would traditional eyewear, perspiration still reaches the eyes, causing the above described problems. Another attempted solution involves placement of an absorbent pad between the forehead and the eyewear. Such a system is commercially available as the ROTOSHIELD™ from Ektelon, Inc. The ROTOSHIELD™ absorbent pad, however, is designed only to absorb perspiration, not to facilitate evaporation, thus having limited effectiveness.

What is clearly needed, therefore, is a system affording eye protection while simultaneously preventing perspiration from interfering with a sports participant's vision.

SUMMARY OF THE INVENTION

I have invented protective eyewear that protects the wearer's eyes as well as simultaneously prevents the migration of perspiration into the wearer's facial region during rigorous athletic activity.

The eyewear is based upon a standard pair of conventional prescription glasses, protective eyewear, or sunglasses. The invention comprises a frame, at least a single lens, a pair of rearwardly extending bows attached to the frame, and a brow bar. The brow bar is designed to substantially match the contours of the forehead of the wearer. An absorbent insert is mounted in the brow bar to directly contact the wearer's forehead and soak up perspiration transpired by the wearer. The brow bar further comprises a plurality of openings to expose portion of the absorbent insert to the air to allow perspiration to evaporate following being absorbed by the insert.

In a preferred embodiment, the absorbent insert is open cell foam that is replaceable in the brow bar.

DETAILED DESCRIPTION OF THE INVENTION INCLUDING A BEST MODE

Figure 1:
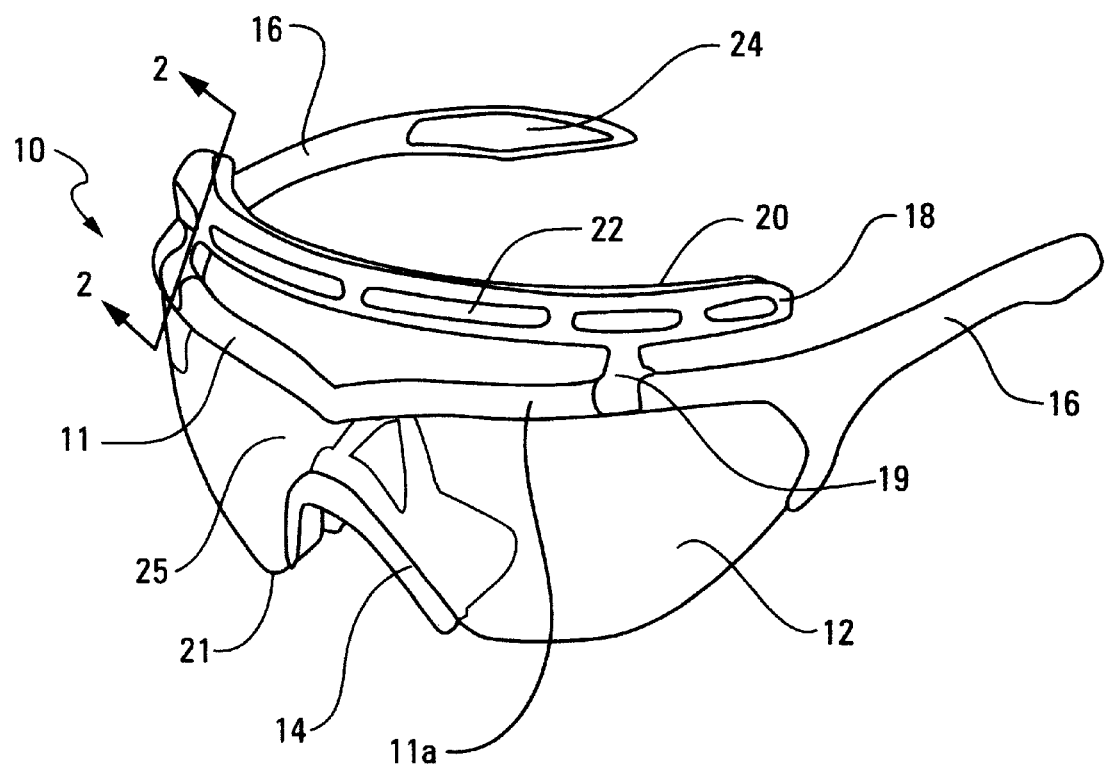
FIG. 1 is a perspective view of a first embodiment of the invention.
Figure 2:
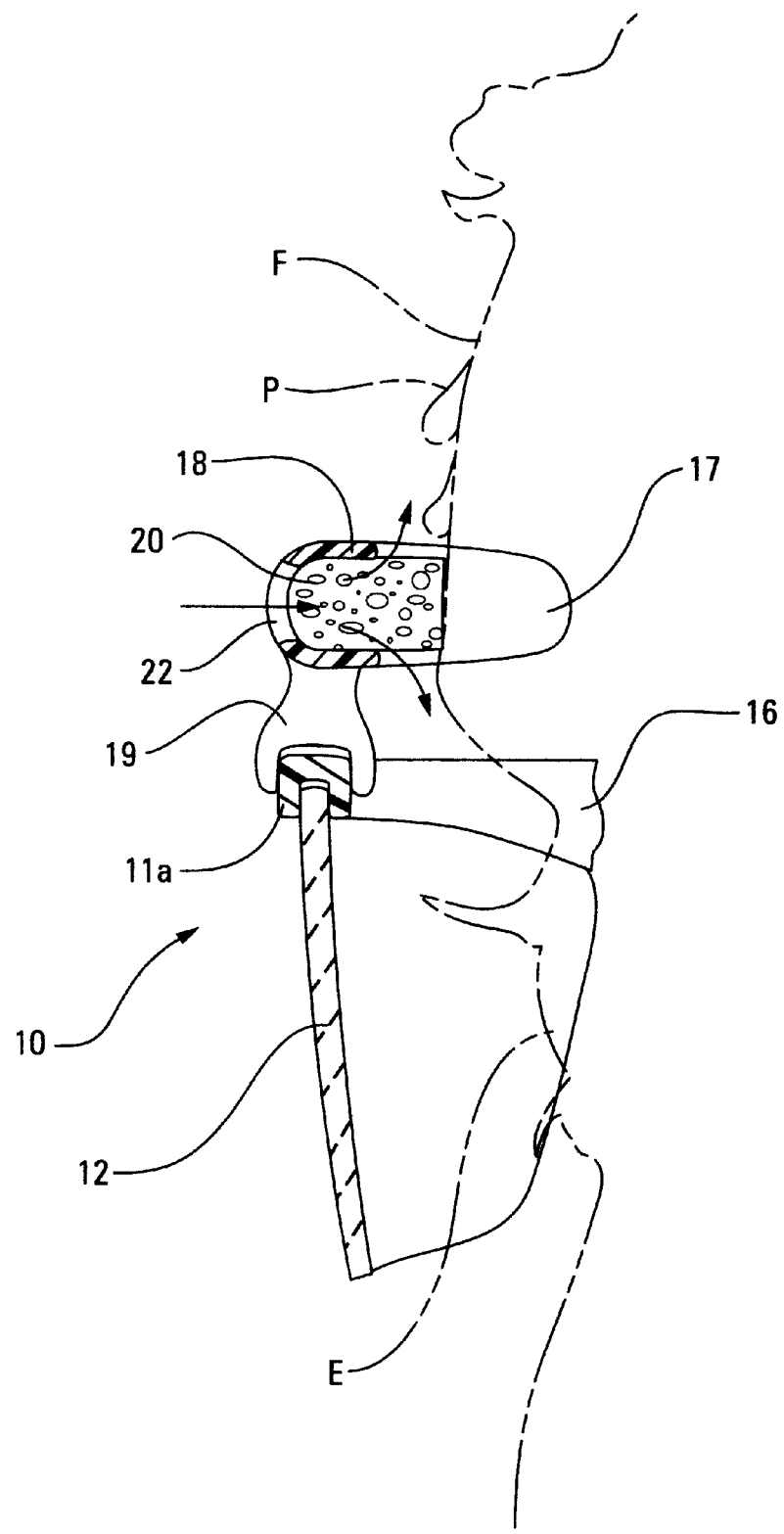
FIG. 2 is a cross section taken along line 2—2 in FIG. 1.
Figure 3:
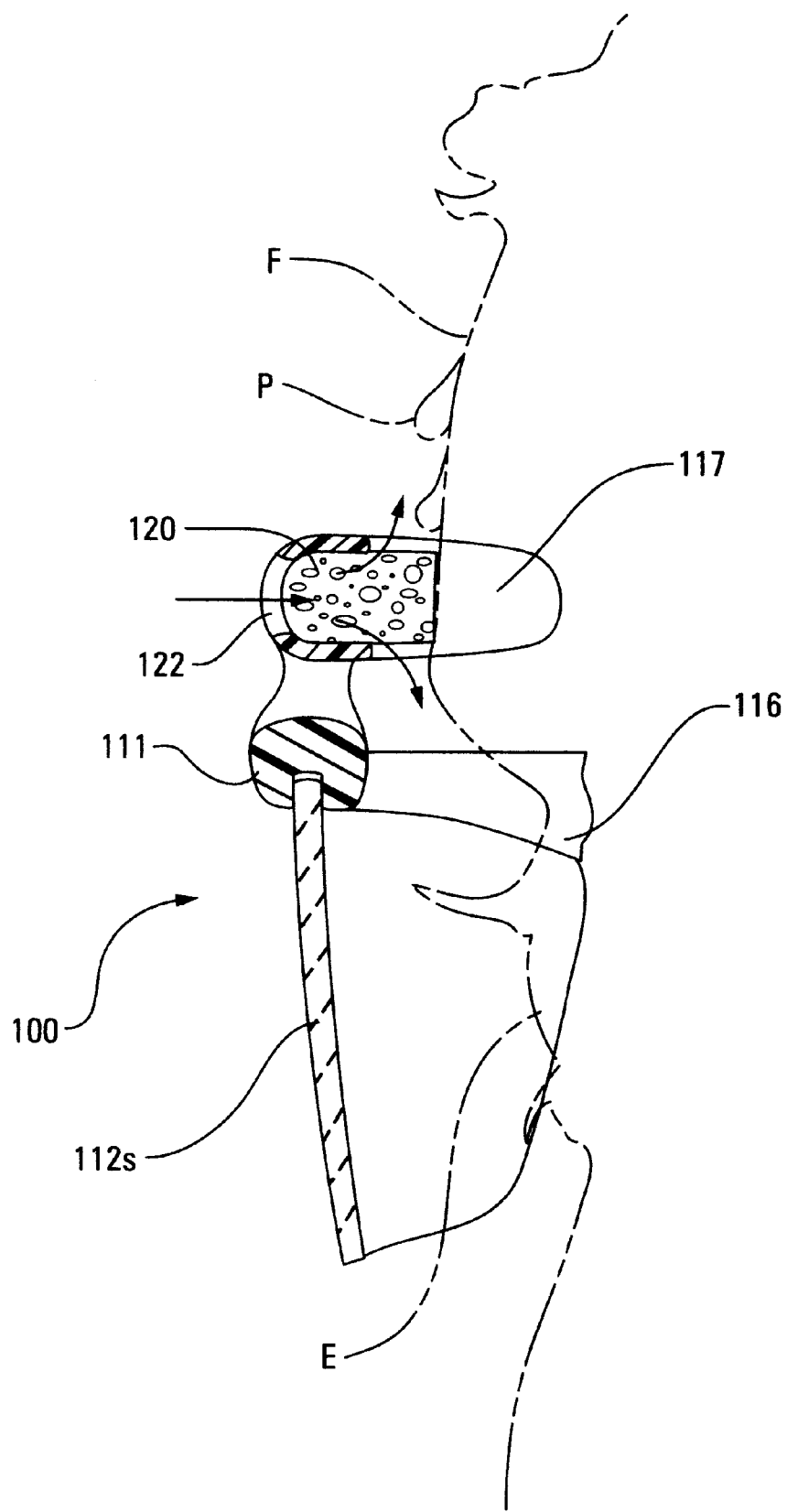
FIG. 3 is a cross section of a second embodiment of the invention taken along line 3—3 in FIG. 4.

Nomenclature
10 Eyewear
11 Frame
11a Top Edge
12 Lens
14 Nosepiece
16 Bow
17 Open Channel
18 Brow Bar
19 Supporting Post
20 Absorbent Insert
21 Inside Edge of Lens
22 Evaporation Window
24 Grip Material
25 Bridge
100 Eyewear
111 Frame
112r Right Lens
112s Left Lens
114 Extension of Frame Nosepiece
116 Bow
117 Open Channel
118 Brow Bar
119 Supporting Post
120 Absorbent Insert
122 Evaporation Window
124 Grip Material
125 Bridge
200 Eyewear
211 Frame
212r Right Lens
212s Left Lens
214 Nosepiece
216 Bow
218 Brow Bar
219 Supporting Post
220 Absorbent Insert
221 Inside Edge of Lens
222 Evaporation Window
224 Grip Material
225 Bridge
300 Eyewear
311 Frame
312 Lens
314 Nosepiece
316 Bow
318 Brow Bar
319 Supporting Post
320 Absorbent Insert
321 Inside Edge of Lens 322 Evaporation Window
324 Grip Material
325 Bridge
400 Eyewear
411 Frame
412 Lens
414 Nosepiece
416 Bow
418 Brow Bar
419 Supporting Post
420 Absorbent Insert
421 Inside Edge of Lens
422 Evaporation Window
424 Grip Material
425 Bridge
500 Eyewear
511 Frame
511a Top Edge
512 Lens
514 Nosepiece
516 Bow
518 Brow Bar
520 Absorbent Insert
521 Inside Edge of Lens
522 Evaporation Windows
524 Grip Material
525 Bridge
E Eye
F Forehead
P Perspiration Construction Referring to FIGS. 1 and 2, a first embodiment of the athletic eyewear 10 includes a single lens 12 of a size sufficient to span the width of a human face, including the eyes E. The eyewear 10 may be selected from any of the various conventional eyewear, including prescription glasses, protective eyewear and sunglasses. The eyewear 10, 100, 200, 300, 400, 500 shown in FIGS. 1–8 is a pair of sunglasses.

Lenses

The lenses 12, 112r, 112s, 212r, 212s, 312, 412, 512 can be formed from any of the convention materials used in the construction of reading glasses, prescription glasses, protective eyewear or sunglasses. Such materials include specifically, but not exclusively, transparent materials such as polycarbonates, polyolefins and glass.

Figure 4:
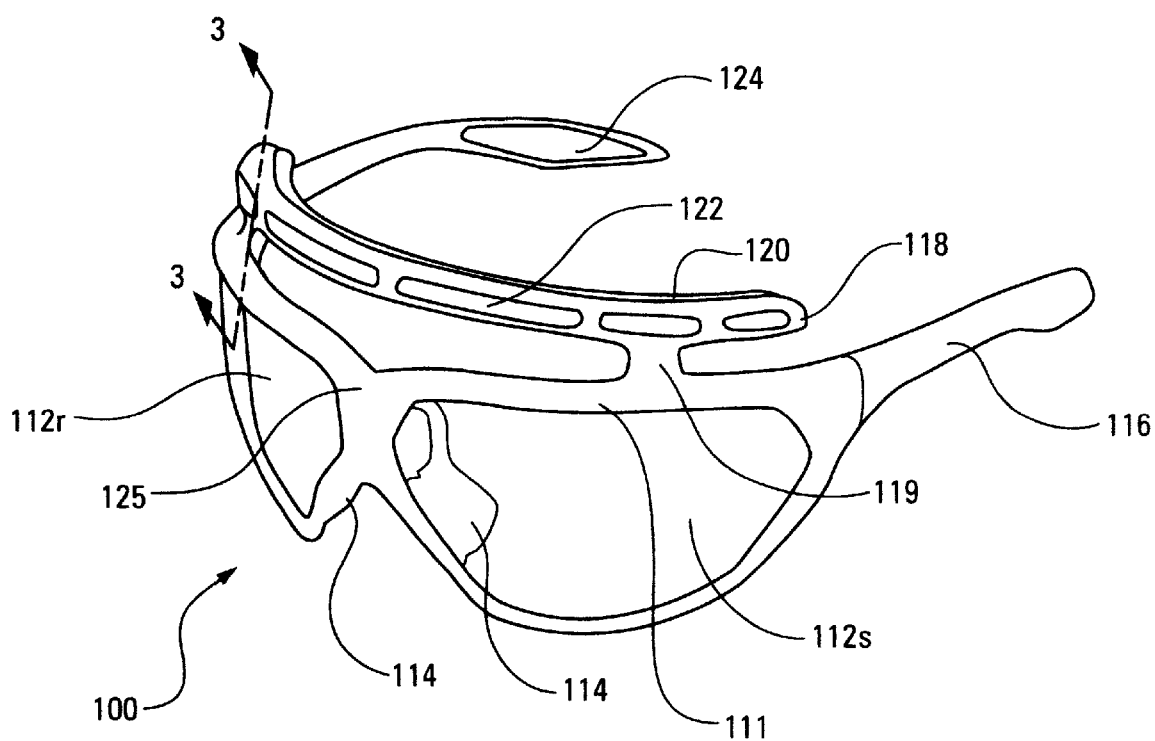
FIG. 4 is a perspective view of the embodiment shown in FIG. 3.
Figure 5:
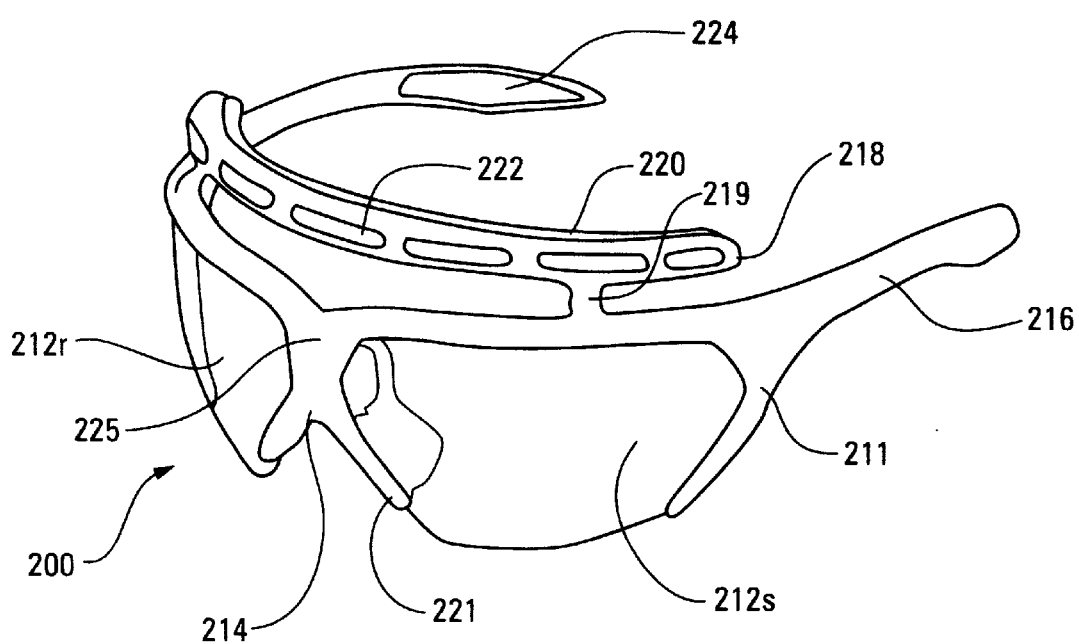
FIG. 5 is a perspective view of a third embodiment of the invention.

The lenses 112r, 112s can be configured into substantially any desired shape from separate right 112r, and left 112s, oval lenses as shown in FIG. 4 or separate trapezoidal lenses 212r, 212s as shown in FIG. 5. In a preferred embodiment, the lenses 12, 312, 412, 512 are formed of a single sheet of material as shown in FIGS. 1, 6, 7 and 8 wherein the lenses are shaped to create the bridge 25, 125, 225, 325, 425, 525 of the eyewear as shown in FIGS. 1, 6, 7 and 8 respectively. The design options for the lenses 12, 112r, 112s, 212r, 212s, 312, 412, 512 are virtually endless, dependent only upon the contours of a wearer's face and the imagination of the designer.

Nosepiece

As with the lenses 12, 112r, 112s, 212r, 212s, 312, 412, 512, the nosepiece 14, 114, 214, 314, 414, 514 can be selected from any of the conventional nosepieces known in the industry, from a simple insert attached to the inside edge 21, 221, 321, 421, 521 of each respective lens 12, 212r, 212s, 312, 412, 512 to an extension 114 of the frame 111 that acts as a nosepiece, as shown in FIG. 4, to an elaborate assembly of a supple pad (not shown) rotatably mounted within an adjustable post (not shown). The nosepiece 14, 214, 314, 414, 514 is formed from an elastomeric material such as a low durometer rubber or thin plastic which includes a longitudinal channel (not shown) for accommodating insertion of an inside edge portion 21, 221, 321, 421, 521 of the lenses 12, 212, 312, 412, 512 and is permanently attached to the lenses 12, 312, 412, 512 by an adhesive (not shown). A particularly well suited nosepiece 14, 214, 314, 414, 514 is one which is capable of conforming to the contours of a wearer's face under a modest pressure of about two to ten times the normal gravitational force exerted upon the wearer's face by the eyewear.

Bows

As shown in FIGS. 1 and 4–7, standard bows 16, 116, 216, 316, 416, 516 are attached to the frame 11, 111, 211, 311, 411, 511 via hinges (not shown) to form a conventional pair of eyewear. The bows 16, 116, 216, 316, 416, 516 can also be directly attached to the lenses 12, 112r, 112s, 212r, 212s, 312, 412, 512 (not shown). A similar material as used on the nosepiece 14, 314, 414, 514 can be used to cover that portion of each bow 16, 116, 216, 316, 416, 516 which contacts the ears (not shown). Finally, grip material 24, 124, 224, 324, 424, 524 is 0 optionally attachable to the portion of the bows 16, 116, 216, 316, 416, 516 contacting the wearer's head above the portion resting on the wearer's ears. The grip material 24, 124, 224, 324, 424, 524 can be a tacky rubber or elastomeric material. It can also be a hydrophilic rubber that gets tackier when moistened. A hypo-allergenic rubber or polymeric material can also be used. The grip material 24, 124, 224, 324, 424, 524 provides a non-slip grip to help secure the eyewear 10, 100, 200, 300, 400, 500 to the wearer's head (unnumbered).

Frame

Depending on the desired strength and design of the eyewear 10, 100, 200, 300, 400, 500 a conventional frame 11, 111, 211, 311, 411, 511 may be provided to which the lenses 12, 112r, 112s, 212r, 212s, 312, 412, 512, bows 16, 116, 216, 316, 416 and brow bar 18, 118, 218, 318, 418 are attached. As shown in FIG. 4, in an embodiment where the frame extends around the perimeter of the lenses, a nosepiece 114 is formed as an extension of the frame. The frame 11, 111, 211, 311, 411, 511 may be constructed from the various materials commonly used to construct eyewear frames, including various plastics, metals, and composite materials. As discussed in greater detail below, the embodiment shown in FIGS. 1 and 2 provides for a brow bar 18 that is pivotably attached to and extends above the frame 11.

Brow Bar

As shown in FIGS. 1–8, a brow bar 18, 118, 218, 318, 418, 518 is attached to the frame 11, 111, 211, 311, 411, 511. In the embodiment shown in FIGS. 1–7, the brow bar 18, 118, 218, 318, 418 extends upward from the frame 11, 111, 211, 311, 411 by means of supporting posts 19, 119, 219, 319, 419. In the embodiment shown in FIG. 8, the brow bar 518 is part of the top edge 511a of the frame 511 that does not extend upward. In a particularly preferred embodiment, the brow bar 18 is separately molded from and attached to the frame 11. The embodiment shown in FIGS. 1 and 2 has a brow bar 18 that is designed to snap on to the top edge 11a of the frame 11 via the posts 19 in a manner allowing the position of the brow bar 18 to pivotably adjust to conform to anatomical differences in different sized wearers. In the embodiment shown in FIG. 1, the brow bar 18 is attached to the top edge 11a of the frame 11 by means of two posts 19 that are of the same length. This is required to allow pivotability of the brow bar 18 about the top edge 11a of the frame 11. Alternatively, a pivotable brow bar 18 could be achieved using additional numbers of posts 19 having the same length pivotably attached to a top edge 11a of the frame 11 that is straight (not shown). In another embodiment (not shown), the separately formed brow bar 18 is rigidly attached to the frame 11 via conventional means such as screws (not shown), or gluing (not shown). Alternatively, the brow bar 118, 218, 318, 418 can be an integral, extended part of the frame 111, 211, 311, 411 as shown in FIGS. 3–7. The brow bar 18, 118, 218, 318, 418 may be constructed from the various materials commonly used to construct eyewear frames, including various plastics, metals and composite materials. When the eyewear 10, 100, 200, 300, 400 is worn during an activity the brow bar 18, 118, 218, 318, 418 extends upward above the wearer's eyebrows to contact the wearer's forehead F. A plurality of evaporation windows 22, 122, 222, 322, 422, 522 facing away from the wearer's face is provided to facilitate evaporation of absorbed perspiration P as more fully discussed below. The side of the brow bar 18, 118, 218, 318, 418, 518 nearest the wearer's forehead F is preferably constructed in an open channel 17 (not shown in FIGS. 1, 4–8) as discussed more fully below.

Absorbent Insert

The brow bar 18, 118, 218, 318, 418, 518 is configured and arranged to accept an absorbent insert 20, 120, 220, 320, 420, 520 which is designed to directly contact the wearer's forehead F. The absorbent insert 20, 120, 220, 320, 420, 520 extends from the brow bar 18, 118, 218, 318, 418, 518 toward the wearer's forehead F, and will contact the wearer's forehead F when the eyewear 10, 100, 200, 300, 400, 500 is properly worn. The absorbent insert 20, 120, 220, 320, 420, 520 in a preferred embodiment is made of an open cell foam material. Such a material is preferred due to its ability to quickly absorb perspiration P, while facilitating evaporation. This phenomenon is known as wicking. Other suitable materials, however, also exist, such as chamois-type material (natural or synthetic) and terry cloth. Thus, through a strenuous event, replacement of the insert 20, 120, 220, 320, 420, 520 is normally not required due to perspiration not being retained. When replacement is required, the open channel 17 configuration of the brow bar 18, 118, 218, 318, 418, 518 allows a quick and easy change. In a preferred embodiment, as shown in FIGS. 1–8, the absorbent insert 20, 120, 220, 320, 420, 520 is firmly held in place by the open channel 17. Additional securing is achieved by the absorbent insert 20, 120, 220, 320, 420, 520 being forced against the wearer's forehead F during wear. Alternative securing means are also contemplated by and therefore within the scope of the invention. Such alternative securing means include, but are not limited to hook-and-loop fasteners (not shown), snaps (not shown) embedded in the absorbent insert 20, 120, 220, 320, 420, 520 and gluing (not shown).

Evaporation Windows

Figure 6:
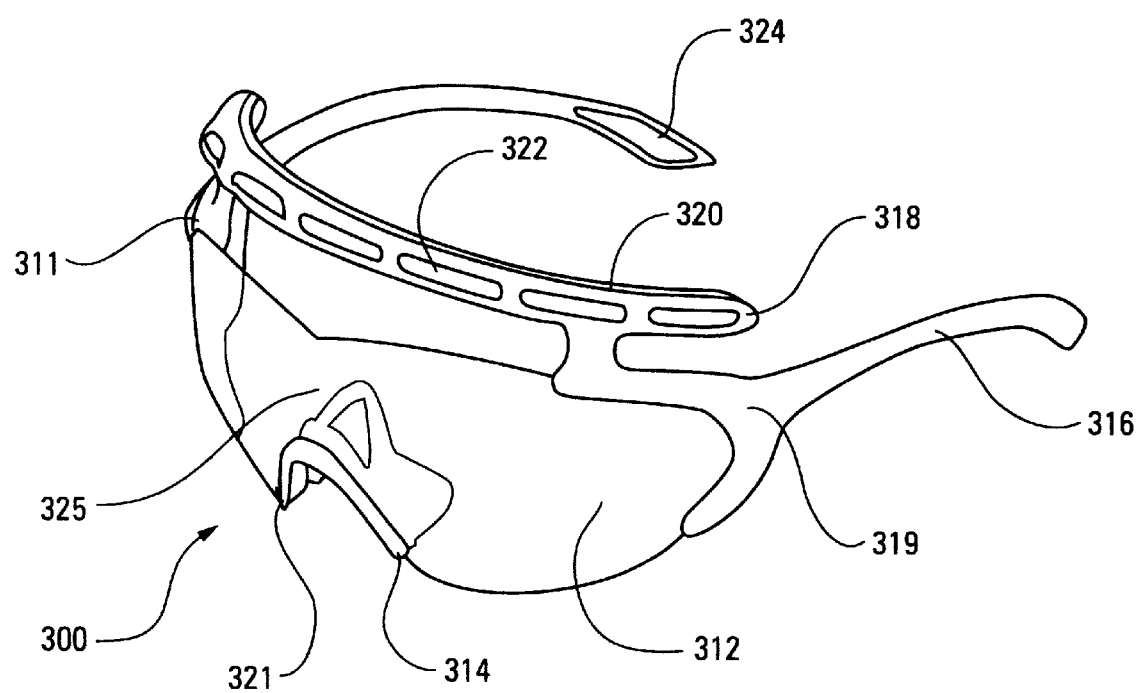
FIG. 6 is a perspective view of a fourth embodiment of the invention.
Figure 7:
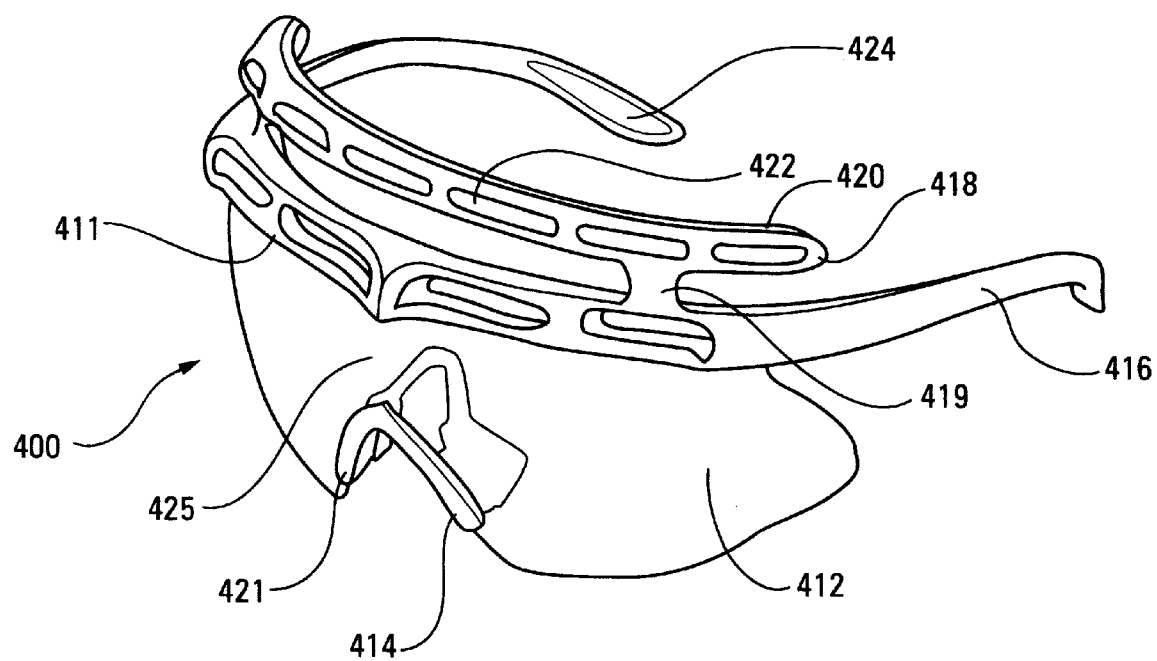
FIG. 7 is a perspective view of a fifth embodiment of the invention.
Figure 8:
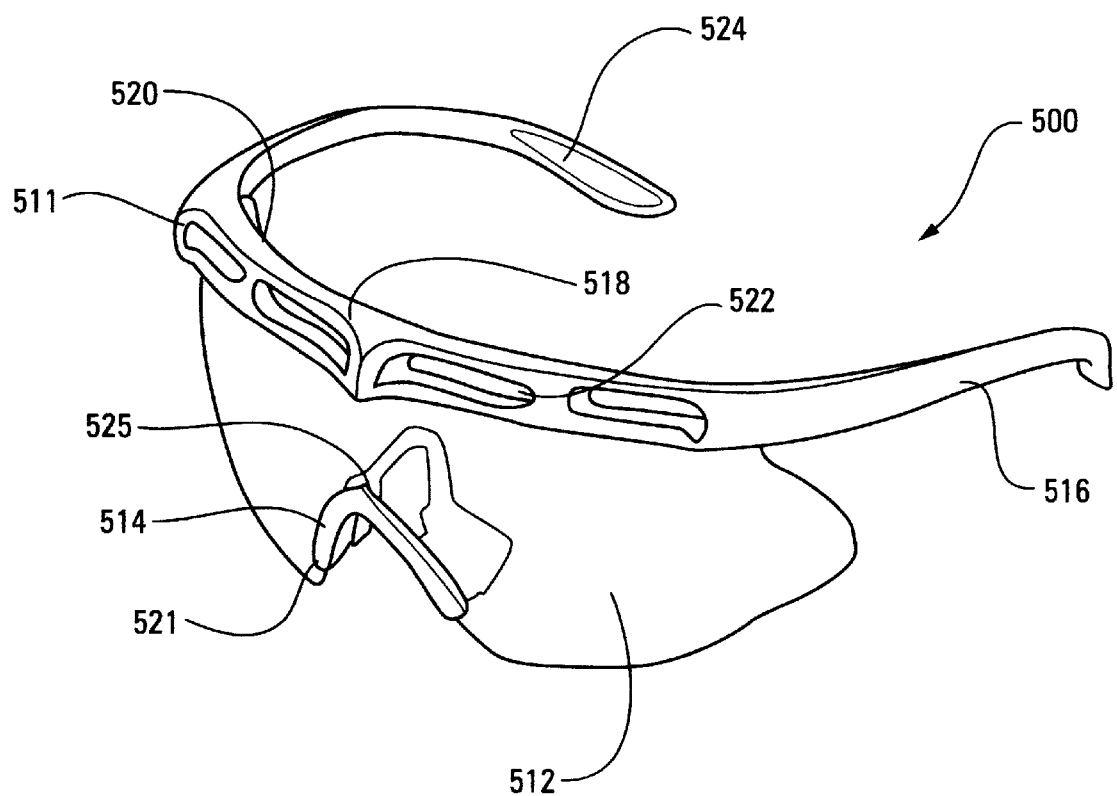
FIG. 8 is a perspective view of a sixth embodiment of the invention.

As shown in FIGS. 1 and 4–8, the brow bar 18, 118, 218, 318, 418, 518 is provided with a plurality of evaporation windows 22, 122, 222, 322, 422, 522. The evaporation windows 22, 122, 222, 322, 422, 522 extend through the brow bar 18, 118, 218, 318, 418, 518 in a manner allowing maximum exposure of the absorbent insert 20, 120, 220, 320, 420, 520 to the air, thus facilitating evaporation of absorbed perspiration P. The open nature of the brow bar 18, 118, 218, 318, 418, 518 allows maximum exposure of the absorbent insert 20, 120, 220, 320, 420, 520 to the air. As shown in FIGS. 1, 4 and 8, in a particularly preferred embodiment, the number of evaporation windows 22, 122, 522 can be relatively few in number, while being relatively large in surface area. Alternatively, as shown in FIGS. 5–7, a relatively large number of evaporation windows 222, 322, 422 may also be used, which are relatively small in surface area.

Appearance

While several different embodiments are shown in FIGS. 1–7, the spirit and scope of the appended claims should not be limited to the description of the preferred versions contained herein. Many other versions are also possible. For example, where different parts and materials are involved, different colors could be used to give a "designer look" to the present invention. Likewise, in embodiments where the frame and brow bar are integrally molded, modern injection molding technology allows different colors to be integrally molded together. The evaporation windows 22, 122, 222, 322, 422, 522 could have a wide variety of shapes, numbers and sizes. The frame 11, 111, 211, 311, 411, 511 could be made in a thin and sporty manner or a thick and athletic manner without departing from the scope of the invention.

What is claimed is:

1. Protective eyewear, comprising:
   (a) a frame having left and right sides and a top;
   (b) a lens coupled with the frame;
   (c) a pair of rearwardly extending bows attached proximate the right and left sides of the frame so as to form a pair of conventional eyewear;
   (d) a brow bar attached to the frame so as to contact a wearer's forehead and having a plurality of openings for allowing airflow therethrough; and
   (e) an absorbent insert attached to the brow bar and extending rearwardly from the brow bar such that the absorbent insert is in fluid communication with airflow through the openings in the brow bar.

2. The protective eyewear of claim 1, wherein the brow bar is attached to the frame so as to contact the wearer's forehead above the wearer's eyebrows.

3. The protective eyewear of claim 1 wherein the means to attach the absorbent insert are replaceable means.

4. The protective eyewear of claim 3 wherein the replaceable means to attach the absorbent insert further comprises an open channel facing toward the wearer's forehead.

5. The protective eyewear of claim 1 wherein the absorbent insert is open cell foam.

6. The protective eyewear of claim 1, wherein the brow bar is pivotably attached to the frame for pivoting forward and rearward relative to the frame by means of two posts having the same length.

7. The protective eyewear of claim 6 wherein the means to attach the absorbent insert are replaceable means.

8. The protective eyewear of claim 6 wherein the absorbent insert is open cell foam.

9. The protective eyewear of claim 1, further comprising the brow bar fixedly attached to the frame.

10. The protective eyewear of claim 9 wherein the means to attach the absorbent insert are replaceable means.

11. The protective eyewear of claim 9 wherein the absorbent insert is open cell foam.

12. The protective eyewear of claim 1 wherein the brow bar is integrally formed with the frame.

13. The protective eyewear of claim 12 wherein the means to attach the absorbent insert are replaceable means.

14. The protective eyewear of claim 12 wherein the absorbent insert is open cell foam.

* * * * *

UNITED STATES PATENT AND TRADEMARK OFFICE
CERTIFICATE OF CORRECTION

| | |
|---|---|
| PATENT NO. | : 6,257,719 B1 |
| DATED | : July 10, 2001 |
| INVENTOR(S) | : Pavlak |

Page 1 of 1

It is certified that error appears in the above-identified patent and that said Letters Patent is hereby corrected as shown below:

<u>Column 4,</u>
Line 23, replace "524 is 0 optionally" with -- 524 is optionally --

Signed and Sealed this

Nineteenth Day of March, 2002

Attest:

JAMES E. ROGAN
*Director of the United States Patent and Trademark Office*

*Attesting Officer*